United States Patent [19]

Mobilio

[11] Patent Number: 5,484,806
[45] Date of Patent: Jan. 16, 1996

[54] PHOSPHOLIPASE $A_2$ INHIBITORS

[75] Inventor: Dominic Mobilio, Franklin Park, N.J.

[73] Assignee: American Home Products Corporation, Madison, N.J.

[21] Appl. No.: 439,061

[22] Filed: May 8, 1995

Related U.S. Application Data

[62] Division of Ser. No. 313,978, Sep. 28, 1994, Pat. No. 5,428,058.

[51] Int. Cl.[6] .................. A61K 31/395; C07D 207/22
[52] U.S. Cl. ............................... 514/423; 548/540
[58] Field of Search ........................ 548/540; 514/423

[56] References Cited

U.S. PATENT DOCUMENTS

| | | | |
|---|---|---|---|
| 4,874,782 | 10/1989 | Bonjouklian et al. | 548/540 |
| 5,242,945 | 9/1993 | Caufield et al. | 548/540 |

FOREIGN PATENT DOCUMENTS

| | | | |
|---|---|---|---|
| 1276061 | 6/1972 | United Kingdom | 514/423 |
| WO9322305 | 11/1993 | WIPO | 514/423 |

OTHER PUBLICATIONS

Nomura et al., Chem Pharm Bulletin, 34:5188 (1986).
Kataoka et al., Chemical Abstracts, 84:175144m (1976).
Orno et al., Chemical Abstracts, 81:151976w (1974).

*Primary Examiner*—Joseph K. McKane
*Attorney, Agent, or Firm*—Arnold S. Milowsky

[57] ABSTRACT

There are disclosed compounds of the formula:

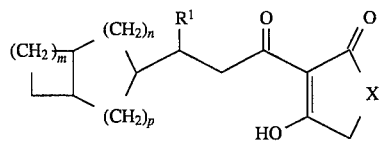

wherein
$R^1$ is hydrogen, alkyl, cycloalkyl, arylalkyl, $-(CH_2)_rCH=CH_2$, $-(CH_2)_sOY$, $-(CH_2)_tCH(OZ)CH_3$, or Ar;
X is O, S, or $NR^2$;
Y and Z are each, independently, hydrogen, alkyl, or $-COR^3$;
$R^2$ and $R^3$ are each, independently, hydrogen, alkyl, or arylalkyl;
Ar is an aryl radical that may be optionally substituted;
m=1–5;
n=0–1;
p=1–9;
r=0–6;
s=2–6; and
t=0–6
or a pharmaceutically acceptable salt thereof which are useful as antiinflammatory agents.

4 Claims, No Drawings

PHOSPHOLIPASE A₂ INHIBITORS

This is a division of application Ser. No. 08/313,978 filed Sep. 28, 1994, now U.S. Pat. No. 5,428,058.

The present invention is directed to certain phospholipase $A_2$ inhibitors and to a method for using them as anti-inflammatory agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980). Cyclooxygenase metabolites are known to participate directly in the inflammatory response [see Higgs et al., Annals of Clinical Research, 16, 287–299 (1984)]. This is through their vasodepressor activities, participation in pain and fever and augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidalive products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J, Immun.*, 215, 115–118 (1980); *Biochem. Biophys. Res. Commun.*, 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature*, 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances as mediators of inflammation and hypersensitivity is extensively reviewed in Bailey and Casey, *Ann. Reports Med. Chem.*, 17, 203–217 (1982).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkyl-arachidonylglycerophosphatidylcholine is acted upon by the $PLA_2$ the generation of platelet activating factor (PAF) is initiated; PAF is pro-inflammatory in its own fight [see Wedmore et al., *Br. J. Pharmacol.*, 74, 916–917 (1981)]. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., *Nature, London*, 278, 456 (1979) and Hirata et al., *Proc. Natn. Acad. Sci., U.S.A.*, 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. Throm. Res.*, 3, 89 (1978)], the inhibition of $PLA_2$ is indicated in the therapeutic treatment of both PAF induced or cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation, as well as in the modulation of PAF-mediated biological processes, such as embryonic implantation, thus making the compounds useful as anti-fertility agents.

This invention provides compounds having the formula

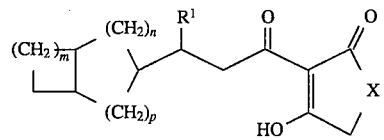

wherein
$R^1$ is hydrogen, alkyl of 1–10 carbon atoms, cycloalkyl of 1–10 carbon atoms, arylalkyl of 4–10 carbon atoms, —$(CH_2)_rCH=CH_2$, —$(CH_2)_sOY$, —$(CH_2)_tCH(OZ)CH_3$, or Ar;

X is O, S, or $NR^2$;

Y and Z are each, independently, hydrogen, alkyl of 1–6 carbon atoms, or —$COR^3$;

$R^2$ and $R^3$ are each, independently, hydrogen, alkyl of 1–6 carbon atoms, or arylalkyl of 4–10 carbon atoms;

Ar is an aryl radical that may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoroalkoxy of 2–7 carbon atoms, amino, dialkylamino of 1–6 carbon atoms per alkyl group, dialkylaminoalkyl of 1–6 carbon atoms per alkyl group, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$;

m=1–5;
n=0–1;
p=1–9;
r=0–6;
s=2–6; and
t=0–6 or a pharmaceutically acceptable salt thereof.

The compounds of this invention possess antiinflammatory activity and inhibit phospholipase $A_2$ ($PLA_2$) in vitro and as such are useful in the treatment and prevention of inflammatory disease states such allergic rhinitis, allergic bronchial asthma, chronic obstructive pulmonary disease, emphysema, acute respiratory distress syndrome, and other naso-bronchial obstructive air-passageway conditions; immediate hypersensitivity reactions, such as allergic conjunctivitis; inflammatory conditions such as those present in rheumatoid arthritis, osteoarthfitis, tendoniris, bursitis, psoriasis, dermatitis, eczema, seborrhea, and related skin disorders; inflammatory bowel diseases, such as Crohn's Disease, irritable bowel syndrome, and the like; and uveitis. The compounds also possess utility in the modulation of biological processes which are effected by platelet activating factor (PAF) such as embryonic implantation and as such are useful as antifertility agents.

The terms alkyl, alkoxy, aminoalkyl, dialkylamino, include both straight chain as well as branched carbon chains. The term "halo" refers to fluoro, chloro, bromo, or iodo.

It is preferred that the aryl radical of Ar and the aryl moiety of the arylalkyl substituent is a phenyl, naphthyl, pyriclyl, quinolinyl, isoquinolinyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, imidazolyl, benzopyranyl, benz[b] thiophenolyl, benzimidazolyl, benzthiazolyl, benzodioxolyl, piperidinyl, morpholinyl, piperazinyl, tetrahydrofuranyl, or pyrrolidinyl radical that is optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoroalkoxy of 2–7 carbon atoms, amino, dialkylamino of 1–6 carbon atoms per alkyl group, dialkylaminoaikyl of 3–12 carbon atoms, hydroxyalkyl of 1–6 carbon atoms, alkoxyalkyl of 2–12 carbon atoms, alkylthio of 1–6 carbon atoms, —SO$_3$H, —PO3H, and —CO$_2$H. It is more preferred that the aryl radical of Ar and the aryl moiety of the arylalkyl substituent is a phenyl, pyridyl, furyl, quinolinyl, isoquinolinyl, piperazinyl, or piperidinyl radical.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, iraconic and benzenesulfonic. The compounds of the invention are capable of forming alkali metal and alkaline earth salts and salts of pharmacologically acceptable cations derived from ammonia or a basic amine. Examples of the latter include but are not limited to cations such as ammonium, mono-, di-, and trimethylammonium, mono-, di-, and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-odimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like. It is preferred that the pharmacologically acceptable salts be formed with 2-amino-(2-hydroxymethyl)-1,3 -propanediol.

The compounds within the scope of the invention by virtue of their configuration, exhibit stereoisomerism. Accordingly, the compounds of the invention include the diastereomers, enantiomorphs, racemates and mixtures thereof.

Of the compounds of this invention, preferred members include those in which m=1–3 and p=1–4; those in which m=1–3, p=1–4, and X is O or S; and those in which m=1–3, p=1–4, X is O or S, and R$^1$ is hydrogen. More preferred members include those in which m=3, n=1, p=2, and X is O or S.

The compounds within the scope of the invention can be prepared by a variety of synthetic routes using conventional methodology. For example, the compounds of this invention in which X is O or S and R$^1$ is hydrogen, alkyl, cycloalkyl, arylalkyl of 4–10 carbon atoms, —(CH$_2$)$_r$CH=CH$_2$, or Ar, can be prepared according to the following scheme from the requisite starting materials that are either commercially available or can prepared by methods described in the literature.

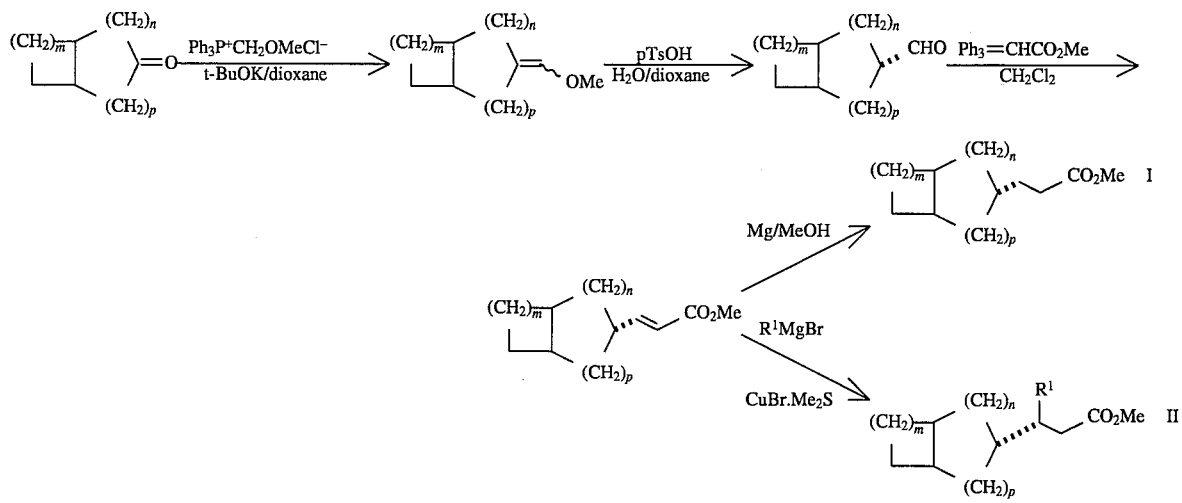

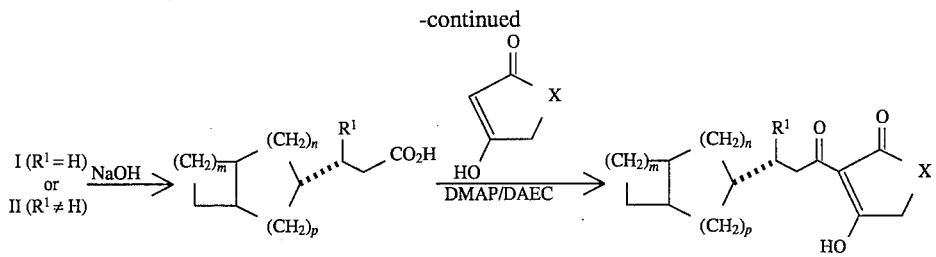

Similarly, compounds in which X is O or S and $R^1$ is $-(CH_2)_sOY$ can be prepared from II [where $R^1$ is $-(CH_2)_rCH=CH_2$] according to the following scheme from the requisite starting materials that are either commercially available or can prepared by methods described in the literature.

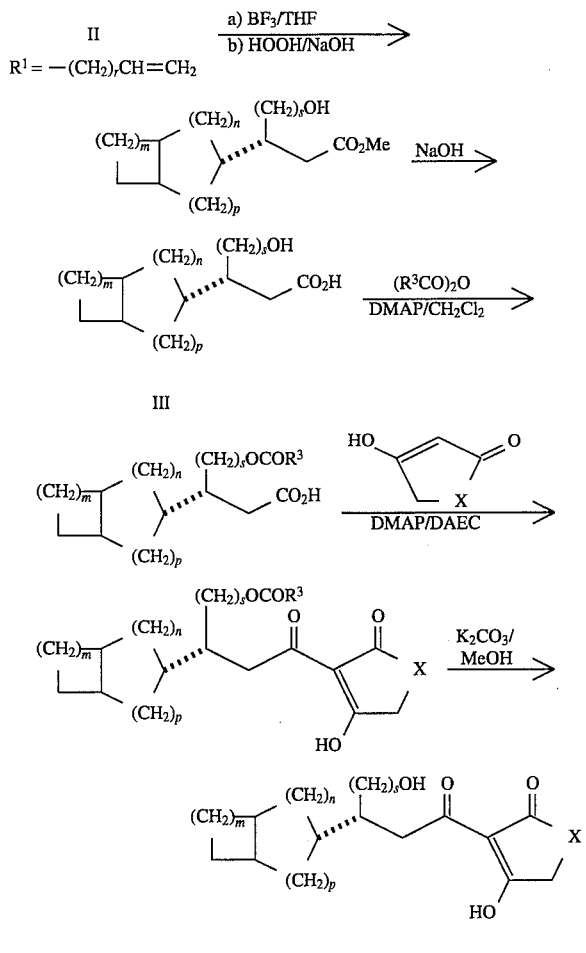

Alternatively, compounds in which X is O or S and $R^1$ is $-(CH_2)_sOH$ can be prepared from III using a silicon protecting group according to the following scheme from the requisite starting materials that are either commercially available or can be prepared by methods described in the literature.

Compounds in which X is O or S and $R^1$ is $-(CH_2)_tCH(OZ)CH_3$ can be prepared from II [where $R^1$ is $-(CH_2)_rCH=CH_2$] according to the following scheme from the requisite starting materials that are either commercially available or can prepared by methods described in the literature.

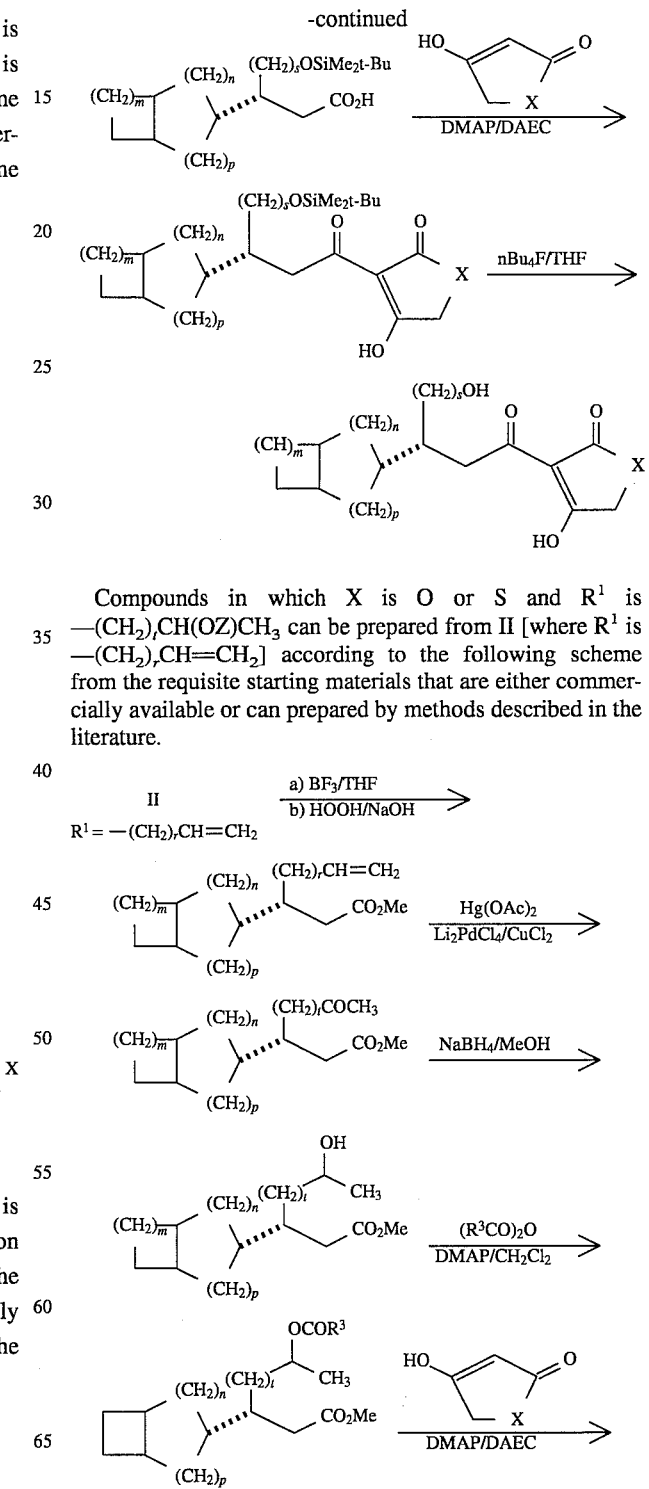

-continued

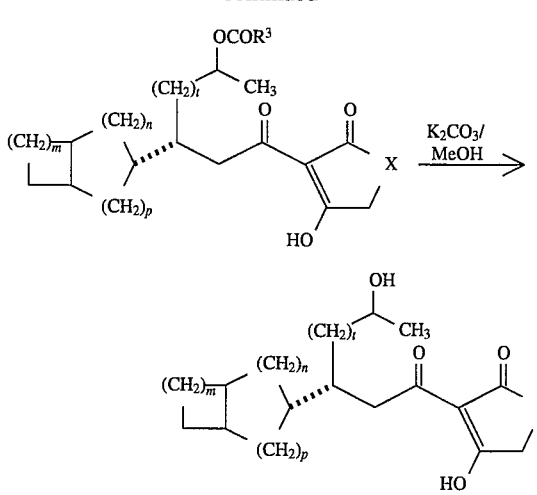

The following scheme shows the preparation of the compounds of this invention in which X is $NR^2$. The compound of formula IV can be prepared from intermediate A, when $R^2$ of A is alkyl, and the compound of formula V can be prepared from intermediate A, when $R^2$ of A is 2,4-dimethoxyphenylmethyl. The requisite starting materials are either commercially available or can prepared by methods described in the literature.

The compounds of the invention, by virtue of their ability to inhibit activity of $PLA_2$ enzyme, are useful in the treatment of conditions mediated by products of the oxidation of arachidonic acid. Accordingly, the compounds are useful as antiinflammatory agents that are indicated in the prevention and treatment of such conditions as allergic rhinitis, allergic bronchial asthma, chronic obstructive pulmonary disease, emphysema, acute respiratory distress syndrome, and other naso-bronchial obstructive air-passageway conditions; immediate hypersensitivity reactions, such as allergic conjunctivitis; inflammatory conditions such as those present in rheumatoid arthritis, osteoarthritis, tendoniris, bursiris, psoriasis, dermatitis, eczema, seborrhea, and related skin disorders; inflammatory bowel diseases, such as Crohn's Disease, irritable bowel syndrome, and the like; and uveitis.

When used as antiinflammatory agents, the compounds of this invention can be administered orally, parenterally, intranasally, intrabronchially, transdermally, rectally, or vaginally. The compounds of this invention can be formulated neat or with a pharmaceutical carrier to a mammal in need thereof.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a

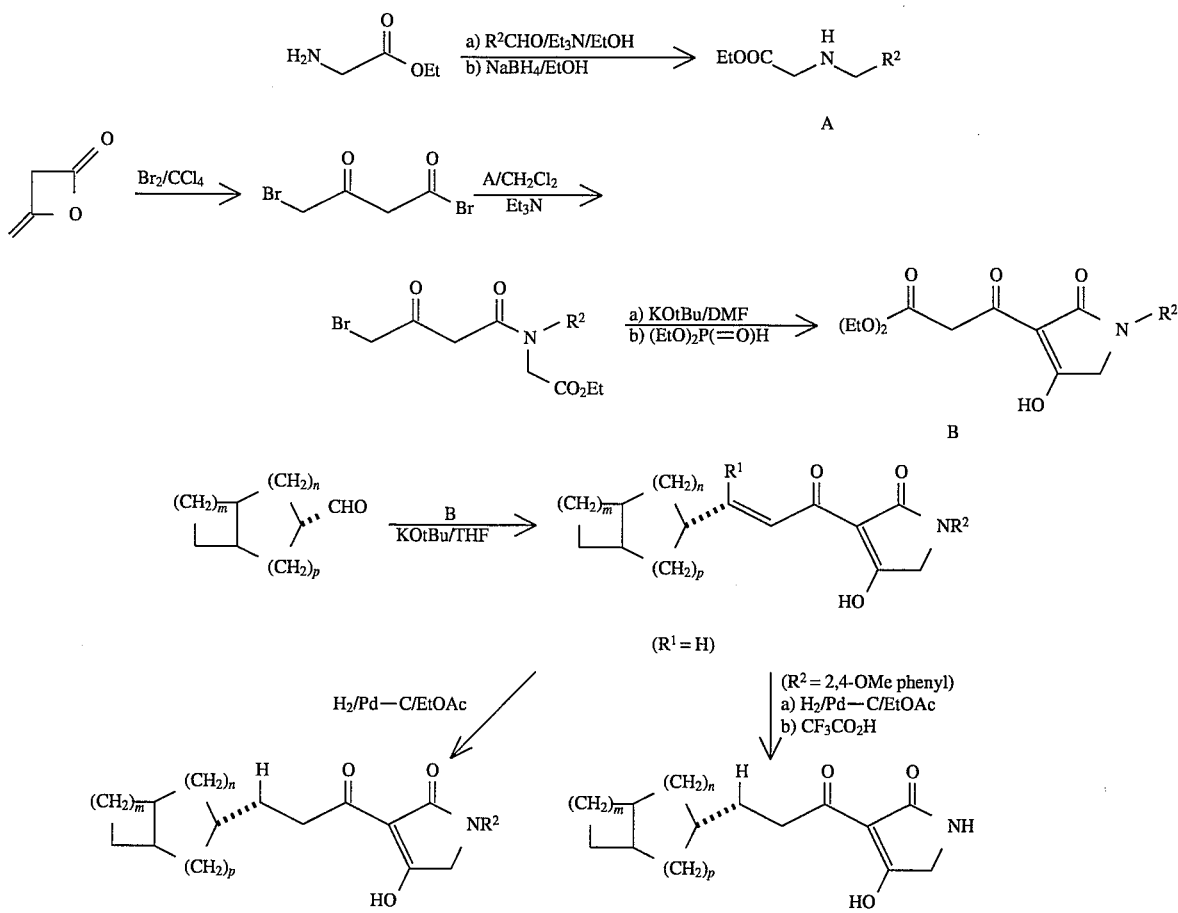

carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected oral daily dosages of active compound would be 0.5 mg/kg–25 mg/kg, and preferably between 1 mg/kg–12.5 mg/kg. For parenteral administration, projected daily dosages of active compound would be 0.05 mg/kg–2.5 mg/kg, and preferably between 0.1 mg/kg–1.25 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The standard pharmacological test procedures, which are described fully in the examples given hereafter, inter alia, demonstrate the ability of the compounds of this invention to act as antiinflammatory agents, by virtue of their ability to inhibit the activity of 5-lipoxygenase and cycloxygenase, and tetradecanoylphorbol acetate (TPA) induced ear edema.

The following examples show the preparation and pharmacological evaluation of representative compounds within the invention.

EXAMPLE 1

3-[3-[(2α,4aα,8aβ)-Decahydro-naphthalene-2-yl]-propionyl]-4-hydroxy-2-(5 H)-furanone

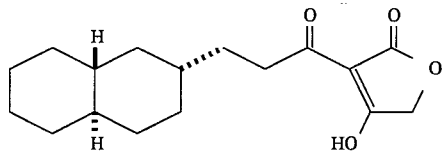

Step a) Preparation of 2-(3H)-4,4a,5,6,7,8-Hexahydronaphthalenone

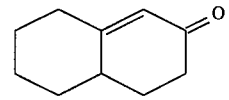

A solution of 1-(N-morpholino)-cyclohexene (200 g, 1.2 mole) in dry 1,4-dioxane (1.2 L) was treated dropwise under nitrogen over 1.5 hours with methyl vinyl ketone (87.5 g, 1.25 mole). After heating under reflux for 4 hours, water (1L) was added and heating continued for 12 hours. After dilution with water (2L) and extraction with ether (4×1L), the combined organic phase was sequentially washed with 3N HCl (3×500 mL), saturated aqueous sodium bicarbonate (2×200 mL), water (500 mL), and saturated brine (400 mL). The ether phase was dried over magnesium sulfate, evaporated in vacuo to a crude amber oil (180 g), and partially purified by vacuum distillation. The oil was dissolved in heptane, filtered, and evaporated in vacuo to a residue which was twice crystallized from heptane at −80° C. The clear liquid (55 g) was further purified by vacuum distillation, bp. 120°–121° C./1 mm Hg, (45 g) and flash column chromatography on silica gel (75:1 ratio) by gradient elution with light petroleum ether/ethyl acetate, 20:1→3:1 which afforded the title compound as a clear colorless oil (19 g, 19% yield).

$^1$H NMR (CDCl$_3$, 400 Mhz) δ: 5.79 (d, J=0.62 hz, 1H), 2.24–2.45 (m, 3H), 2.28 (ddd, J=16.2, 12.7, 5.0 hz, 1H), 2.18 (td, J=13.6, 5.4 hz, 1H), 2.07 (ddd, J= 14.9, 10.0, 5.0 hz, 1H), 1.79–1.98 (M, 3H), 1.62 (m, 1H), 1.47 (qt, J=12.9, 3.3 hz, 1H), 1.37 (qt, J=12.9, 3.3 hz, 1H), 1.19 (qd, J=12.9, 3.7 hz, 1H)

$^{13}$C NMR (CDCl$_3$, 100 Mhz) δ: 193.74 (1C), 167.12 (1C), 124.01 (1C), 37.65 (1C), 36.28 (1C), 35.31 (1C), 34.21 (1C), 28.95 (1C), 26.71 (1C), 25.31 (1C)

MS (EI), m/z (rel. intensity)=150 (M$^+$, 60), 122 (100), 108 (25), 94 (40), 79 (30) IR (Film)ν: 2930, 2860, 1670, 1620, 1450, 1260, 1205, 1160, 905,860cm$^{-1}$.

Step b) Preparation of (4aα, 8aβ)-2-Decalone

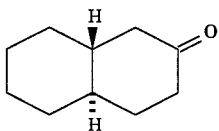

Double distilled liquid ammonia (1.5L) was treated under nitrogen at −78° C. with lithium wire (12.45 g, 1.78 moles). After all the lithium dissolved, a mixture of 2-( 3H)-4,4a, 5,6,7,8-hexahydronaphthalenone (17.8 g, 118.6 mmol) and t-butanol (6.89, 93 mmol) was added dropwise as a solution in dry tetrahydrofuran (475 mL) (4 mL/mmol). After 3 hours at −78° C., the excess lithium was destroyed by dropwise titration with 2,3-dimethyl-1,3-butadiene to the disappearance of the blue color, and the excess solvent allowed to evaporate overnight. With cooling, water (1L) was carefully added and the aqueous phase extracted with ether (3×700 mL). The combined organic layer was sequentially washed with 2N HCl (250 mL) and distilled water (2×250 mL), dried over magnesium sulfate, filtered, and evaporated in vacuo to a crude amber oil (16.6 g, 94% recovery). Purification by vacuum distillation afforded the title compound as a clear oil (13.76 g) containing approximately 10% of the further reduced trans-2-decalinol as determined by $^1$H and $^{13}$C NMR.

$^1$H NMR (CDCl$_3$, 400 MHz) δ: 2.25–2.38 (m, 3H), 2.04 (dd, J=12.6, 11.6 hz, 1H), 1.89–1.95 (m, 1H), 1.50–1.77 (m, 4H), 0.94–1.42 (m, 7H)

$^{13}$C NMR (CDCl$_3$, 100 MHz) δ: 211.43 (1C), 48.48 (1C), 43.21 (1C), 41.54 (1C), 41.45 (1C), 34.09 (1C), 33.52 (1C), 32.57 (1C), 25.99 (1C), 25.48 (1C)

MS (EI), m/z (rel. intensity)=152 (M$^+$, 80), 108 (100), 95 (60), 81 (100), 67 (80) 55 (90)

IR (Film) ν: 2920, 2850, 1715, 1450, 1220, 1165 cm$^{-1}$

Anal. Calcd. for C$_{10}$H$_{16}$O: C, 78.90; H, 10.59
Found: C, 71.78; H, 9.60.

Step c) Preparation of (4aα, 8aβ)-Decahydro-2-(methoxymethlene)naphthalene

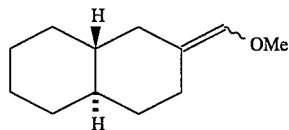

A suspension of methoxymethyltriphenylphosphonium chloride (68.4 g, 200 mmol) in dry 1,4-dioxane (600 mL) was treated with potassium t-butoxide (22.4 g, 200 mmol) at 20 C. under N$_2$. After 1.5 hours, (4aα, 8aβ)-2-decalone (13.13 g, 86 mmol) was added and stirring continued for 1 hour at 20° C., followed by 1 hour at 100° C. After dilution with ether (3L), the mixture was extracted sequentially with water (500 mL) and saturated brine (3×200 mL). The organic phase was dried over magnesium sulfate, twice filtered through a silica gel pad, and evaporated to afford 45 g of the title compound as a dioxane-containing amber oil.

Step d) Preparation of (2α, 4aα, 8aβ)-Decahydro-2-naphthalenecarboxaldehyde

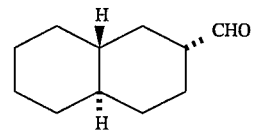

A dioxane solution of (4aα, 8aβ)-decahydro-2-(methyoxymethylene)naphthalene (45 g, 86 mmol) in 1,4-dioxane (1L) and water (200 mL) was treated with 4-methylbenzenesulfonic acid (1.9 g, 10 mmol and heated under reflux for 16 h. The reaction volume was concentrated in vacuo, the residue diluted with ether (4L) and extracted sequentially with water (300 mL), 50% saturated sodium bicarbonate, water (100 mL), and 50% saturated brine (100 mL). The organic phase was dried over magnesium sulfate, filtered through a plug of silica gel and evaporated in vacuo to a light amber oil (37 g). The aldehyde was purified by flash column chromatography on silica gel (1 kg, 75:1 ratio) and eluted with petroleum ether-ether (98:2) to afford the title compound as a clear light oil, (5.0 g, 35% yield).

$^1$H NMR (DMSO-d$_6$, 400 Mhz) δ: 9.60 (bs, 1H, minor isomer), 9.51 (d, J=1.3 hz, 1H, major isomer, ratio 23:1), 2.27 (ttd, J=12.0, 3.5, 1.3 hz, 1H), 1.87 (dm, J= 13.0 hz, 1H), 1.75 (dm, J=13.5 hz, 1H), 1.50–1.70 (m, 5H), 1.04–1.28 (m, 3H), 0.78–1.02 (m, 6H)

$^{13}$C NMR (DMSO-d$_6$, 100 Mhz) δ: 204.26 (1C), 49.56 (1C), 42.22 (1C), 41.46 (1C), 33.32 (1C), 33.14 (1C), 32.68 (1C), 32.17 (1C), 25.99 (2C), 25.46 (1C)

MS (EI), m/z (rel. intensity)=182 (M$^+$CO$_2$H, 50), 95 (100), 81 (100), 67 (65). Sample was observed as the air-oxidized acid product. IR (Film) ν: 2910, 2840, 1730, 1685 (CO$_2$H) cm$^{-1}$.

Step e) Preparation of (E,Z)-3-[(2α,4aα,8aβ)-Decahydro-2-naphthalenyl]propenoic acid, methyl ester

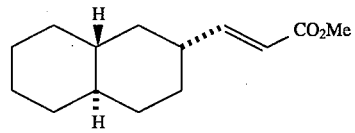

A solution of (2α, 4aα, 8aβ)-decahydro-2-naphthalenecarboxaldehyde (4.3 g, 26 mmol) in methylene chloride (300 mL) was treated at room temperature under nitrogen with methyl triphenylphosphorylidene acetate (8.69 g, 26 mmol) and stirred overnight. After evaporation of the solvent in vacuo and twice trituration and filtration of the residue with petroleum ether-ether (10:1) through a plug of silica gel, the flitrate was evaporated in vacuo affording the title compound as a clear oil (5.2 g, 90% yield) with an E/Z ratio of (10.75/:1). A small amount (~6%) of the (E)-2α, 4aβ, 8aα isomer was present as determined by $^1$H and $^{13}$C NMR.

$^1$H NMR (CDCl$_3$, 400 Mhz) δ: 6.88 (dd, J=15.8, 6.8 hz, 1H), 5.74 (dd, J=15.8, 1.2 hz, 1H), 3.69 (s, 3H), 2.10–2.19 (m, 1H), 1.75 (m, 1H), 1.55–1.68 (m, 6H), 0.81–1.24 (m, 9H)

$^{13}$C NMR (CDCl$_3$, 100 Mhz) δ: 167.49 (1C), 154.37 (1C), 118.32 (1C), 51.31 (1C), 42.69 (1C), 42.49 (1C), 40.66 (1C), 38.91 (1C), 33.81 (1C), 33.66 (1C), 33.19 (1C), 31.58 (1C). 26.53 (1C), 26.50 (1C)

MS (EI), m/z (rel. intensity)=222 (M$^+$, 30), 148 (60), 87 (100) IR (Film) ν: 2910, 2840, 1720, 1650, 1445, 1430, 1170, 1040, 980 cm$^{-1}$.

Step f) Preparation of 3-[(2α,4aα,8aβ)-Decahydro-2-naphthalenyl]propionic acid, methyl ester

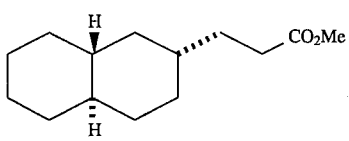

A solution of (E,Z)-3-[(2α,4aα,8aβ)-decahydro-2-naphthalenyl]-propenoic acid, methyl ester (10.75:1, E/Z) (5 g, 22.5 mmol) in methanol (300 mL) was treated under nitrogen at −15° C. with magnesium turnings (6 g, 250 mmol), then allowed to warm to room temperature with stirring overnight. After evaporation of the solvent in vacuo and trituration and filtration of the residue with ether, the ether flitrate was washed with 2N HCl (200 mL), and saturated brine (100 mL). The organic phase was dried over magnesium sulfate, filtered through a plug of silica gel, and evaporated in vacuo, affording the title compound as a clear oil (3.75 g, 74% yield) with ~90% purity as determined by $^1$H and $^{13}$C NMR.

$^1$H NMR (CDCl$_3$, 400 Mhz) δ: 3.65 (s, 3H), 2.31 (dd, J=8.1, 7.7 hz, 2H), 1.65– 1.73 (m, 3H), 1.48–1.60 (m, 6H), 1.20–1.35 (m, 3H), 0.86–1.00 (m, 6H), 0.63 (q,J=11.6 hz, 1H)

$^{13}$C NMR (CDCl$_3$, 100 Mhz) δ: 174.52 (1C), 51.38 (1C), 43.23 (1C), 42.83 (1C), 40.41 (1C), 37.28 (1C), 34.04 (IC), 33.78 (1C), 33.72 (1C), 32.87 (1C), 32.31 (1C), 31.68 (1C), 26.63 (1C), 26.56 (1C)

MS (EI), m/z (rel. intensity)=224 (M$^+$, 40), 146 (100), 95 (100) IR (Film) v:2910, 2840, 1740, 1445, 1165 cm$^{-1}$.

Step g) Preparation of 3-[(2α,4aα,8aβ)-Decahydro-2-naphthalenyl]-propionic acid

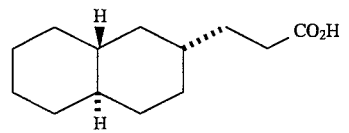

A solution of methyl 3-[(2α, 4aα, 8aβ)-decahydro-2-naphthalenyl]-propionate (3.3 g, 14.7 mmol) in methanol (50 mL) was treated with 2.5N sodium hydroxide (16 mL, 40 mmol) and heated under reflux for 9 hours. Neutralization with 2N HCl (20 mL, 40 mmol) and addition of water (10 mL) afforded after cooling and filtration 2.96 g (95% yield) of the title acid as a white solid, m.p. 85°–88° C.

$^1$H NMR (DMSO-d$_6$, 400 Mhz) δ: 11.94 (s, 1H), 2.18 (dd, J=7.9, 7.5 hz, 2H), 1.59–1.68 (m, 3H), 1.52–1.56 (m, 4H). 1.38 (q, J=7.3 hz, 2H), 1.16–1.27 (m, 3H), 0.78–0.97 (m, 6H), 0.59 (q,J=11.6 hz, 1H)

$^{13}$C NMR (DMSO-d$_6$, 100 Mhz)δ: 174.60 (1C), 42.74 (1C), 42.36 (1C), 40.04 (1C), 36.72 (1C), 33.58 (1C), 33.32 (2H), 32.43 (1C), 31.99 (1C), 31.30 (1C), 26.14 (1C), 26.08 (1C)

MS (El), m/z (rel. intensity)=210 (M$^+$, 10), 192 (5), 151 (30), 148 (70), 95 (100), 81 (70), 67 (45) IR (KBr) v: 3420, 2910, 2840, 1695, 1435, 1225, 1215 cm$^{-1}$ Anal. Calc'd for C$_{13}$H$_{22}$O$_2$: C, 74.24; H, 10.54 Found: C, 73.84; H, 10.19.

Step h) Preparation of 3-[3-[(2α,4aα,8aβ)-Decahydro-2-naphthalenyl]propionyl] -4-hydroxy-2-(5H)-furanone

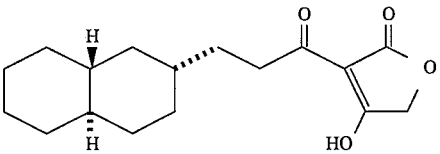

A cooled solution of tetronic acid (0.36 g, 3.6 mmol) in dry methylene chloride (25 mL) was treated with triethylamine (0.79 g, 7.8 mmol) and 4-(dimethylamino)pyridine (0.134 g, 1.1 mmol) and stirred at 0° C. for 0.5 hour. 3-[(2α, 4aα, 8aβ)-Decahydro-2-naphthalenyl]-propionic acid (0.72, 3.4 mmol) followed by 1-( 3-dimethylaminopropyl)-3-ethylcarbodiimide hydrochloride (0.69 g, 3.6 mmol) was added, and the mixture stirred at room temperature under nitrogen overnight.

The reaction was diluted with methylene chloride (300 mL) and extracted with 1N HCl (50 mL). The organic phase was washed with water (2×50 mL), dried over sodium sulfate, and evaporated in vacuo to 800 mg of an amber waxy solid. Crystallization from ethanol afforded after drying in vacuo at room temperature overnight, 240 mg (24% yield) of the title compound as a homogeneous off-white crystalline solid, m.p. 95°–97° C.

$^1$H NMR (CDCl$_3$, 40.0 Mhz) δ: 12.38 (bs, 1H), 4.62 (s, 1.2H major tautomer), 4.50 (s, 0.8H minor tautomer), 2.89 (t, J=8.7 hz, 2H minor tautomer), 2.87 (t, J=8.5 hz, 2H major tautomer), 1.50–1.74 (m, 9H), 1.33 (m, 1H), 1.20 (m, 2H), 0.73–0.95 (m, 6H), 0.63 (m, 1H)

$^{13}$C NMR (CDCl$_3$, 100 Mhz) δ: 198.15 (1C major tautomer), 198.00 (1C, minor tautomer), 192.00 (1C, major tautomer), 191.80 (1C, minor tautomer), 168.00 (1C), 100.02 (1C, major tautomer), 96.60 (1C, minor tautomer), 73.56 (1C, minor tautomer), 68.74 (1C, major tautomer), 43.18 (1C), 42.83 (1C), 40.37 (1C), 37.50 (1C), 34.01 (1C), 33.75 (1C), 33.67 (1C), 32.91 (1C), 32.87 (1C), 32.30 (1C), 26.62 (1C), 26.55 (1C)

MS (EI), m/z (rel. intensity)=292 (M$^+$, 50), 274 (100), 256 (40) IR (KBr)v: 3450, 2910, 2840, 1750, 1640, 1595, 1425, 1030, 1010 cm$^{-1}$ Anal. Calc'd for C$_{17}$H$_{24}$O$_4$: C 69.84, H 8.27 Found: C 70.04, H 8.33.

EXAMPLE 2

3-[3-[(2α,4aα, 8aβ)-Decahydro-naphthalene-2-yl]-propionyl]-4-hydroxy-2 -(5H)-thiophenone

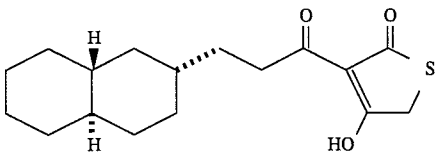

A cooled solution of thiotetronic acid (1.16 g, 10 mmol) in dry methylene chloride (50 mL) was treated with triethylamine (1.93 g, 19 mmol) and 4 -(dimethylamino)pyridine (370 mg, 3 mmol) and stirred at 0° C. for 0.5 hour. 3-[ (2α,4aα,8aβ)-Decahydro-2-naphthalenyl]-propionic acid (1.91 g, 10 mmol) followed by 1-(3-dimethylaminopropyl)-3-ethylcarbodiimide hydrochloride (1.91 g, 10 mmol) was added, and the mixture stirred at room temperature under nitrogen overnight.

The reaction was diluted with methylene chloride (500 mL) and extracted with 1N HCl (100 mL). The organic layer was washed with water (3×100 mL), dried over magnesium sulfate, and evaporated in vacuo to 2.0 g of an amber waxy solid. Crystallization from acetonitrile-ethanol followed by further recrystallization from ethanol afforded, after drying in vacuo at room temperature overnight, 400 mg (14% yield) of the title compound as a homogeneous white crystalline solid, m.p. 77°–79° C.

$^1$H NMR (CDCl$_3$, 400 Mhz) δ: 3.95 (s, 1.6H major tautomer), 3.74 (s, 0.4H minor tautomer), 2.92 (m, 2H), 1.50–1.74 (m, 9H), 1.32 (m, 1H), 1.20 (m, 2H), 0.75–0.97 (m, 6H), 0.64 (m, 1H)

$^{13}$C NMR (CDCl$_3$, 100 Mhz) δ: 200.00 (1C), 199.00 (1C), 191.51 (1C), 110.01 (1C), 43.21 (1C), 42.86 (1C), 40.42 (1C), 37.50 (1C), 35.26 (1C), 34.48 (1C), 34.03 (1C), 33.78 (1C), 33.72 (1C), 32.94 (1C), 31.94 (1C), 26.65 (1C), 26.58 (1C)

MS (EI), m/z (rel. intensity)=308 (M$^+$, 10), 290 (40), 171 (60), 158 (100), 143 (25) IR (KBr) ν: 3440, 2910, 2840, 1675, 1620, 1545, 1450, 860 cm$^{-1}$ Anal. Calcd. for C$_{17}$H$_{24}$O$_3$S: C, 66.20; H, 7.84 Found: C, 66.06; H, 7.71.

EXAMPLE 3

The ability of the compounds of the invention to act as inhibitors of the enzymes 5-lipoxygenase and cyclooxygenase was evaluated in the resident murine peritoneal macrophage standard pharmacological test procedure. This test procedure was carried out as follows.

Resident peritoneal macrophages were collected from female Swiss Webster mice (49 days old, 20–25 gms, Buckshire) by lavaging with 7–8 ml Hanks Balanced Salt Solution (HBSS) without Ca$^{++}$ and Mg$^{++}$ (GIBCO). The lavage fluid from several mice was pooled and centrifuged at 4° C. for 10 minutes at 400 xg. The cell pellet was resuspended in Medium 199 (GIBCO) with HEPES buffer containing 100 μg/ml gentamicin. Two ml of the cell suspension (4×10$^6$ cells) were then plated on 35 mm culture dishes (Nunc).

A macrophage monolayer was established after a 1–1.5 hour incubation of the cells at 37° C. in an atmosphere of 95% O$_2$ and 5% CO$_2$. The monolayers were washed 2x with 2 ml HBDSS, containing Ca$^{++}$ and Mg$^{++}$ after which 2 ml Medium 199 supplemented with 10% freshly thawed heat-inactivated fetal bovine serum and 100 μg/ml gentamicin was added for an overnight incubation.

Residual serum and cellular debris were removed from the monolayers by washing 3x with 2 ml HBSS containing Ca$^{++}$ and Mg$^{++}$. Macrophages were preincubated for 5 minutes with 1 ml serum-free M199 containing 10 μl dimethyl sulfoxide (DMSO) vehicle or test compound prior to cell activation with zymosan (100 Mg/ml) or arachidonic acid (AA) (2 μM). After 2 hours, the supernatants were removed and either assayed for LTC$_4$ and PGE2 by radio-immunoassay (RIA) directly or stored at −20° C. In all cases, results are expressed as ng metabolite/4×10$^6$ cells.

Summary of RIAs used for quantitation of metabolite levels in zymosan or arachidonic acid stimulated mouse macrophage culture media.

| Metabolite | Range of detection (μg/ml) | Metabolite Levels (ng/4 × 10$^6$ cells) (x ± S.E.M..n) |
|---|---|---|
| LTC$_4$ | 0.25–16 | 93.7 ± 9.9 (34) |
| PGE$_2$ | 0.027–20 | 30.90 ± 1.93 (39) |

Calculations: The raw data were converted to ng metabolite/4–10$^6$ cells using a standard curve. Results were then expressed as percent inhibition of zymosan induced, leukotriene or prostaglandin synthesis (control) using the following equation:

$$\% \text{ Inhibition} = \frac{\text{control metabolite level} - \text{sample metabolite level}}{\text{control metabolite level}} \times 100$$

REFERENCE COMPOUNDS: The compounds used are listed below.

IC$_{50}$ values of reference 5-lipoxygenase and/or cyclooxygenase inhibitors.

| | IC$_{50}$ μM (95%) Confidence limits | |
|---|---|---|
| Compound | LTC$_4$ | PGE$_2$ |
| BW 755c | 0.21 | 1.04 |
| | (0.10, 0.42) | (0.73, 1.49) |
| ETYA | 0.44 | 1.26 |
| | (0.36, 0.53) | (0.99, 1.60) |
| Indomethacin | >50 | 0.002 |
| | | (0.001, 0.003) |
| NDGA | 1.87 | 2.15 |
| | (0.22, 15.57) | (1.15, 4.04) |

When tested in this standard pharmacological test procedure, representative compounds of this invention exhibited the following levels of enzyme inhibition:

TABLE I

| Compound of Example No. | Dose μM | PGE$_2$ % Inhibition | LTC$_4$ % Inhibition |
|---|---|---|---|
| 1 | 0.5 | 54 | 59 |
| 2 | 0.1 | −5 | 43 |
| | 0.1 | −23 | 37 |
| | 0.5 | 80 | 92 |
| | 0.5 | 85 | 92 |

The results obtained in this standard pharmacological test procedure showed that the compounds of this invention inhibited 5-lipoxygenase and cycloxygenase, and are therefore useful as antiinflammatory agents.

EXAMPLE 4

Representative compounds of this invention were evaluated in an in vivo standard pharmacological test procedure that measured the effect of the representative compounds on dermal inflammation, as measured by the prevention of tetradecanoylphorbol acetate (TPA) induced ear edema in Webster mice. This test procedure was carried out as follows.

Mice were placed into plastic boxes in groups of six. Eight groups of mice received TPA topically on the right ear. TPA was dissolved in acetone at a concentration of 100 ug/ml. TPA was applied to the right ear by the means of an automatic pipette. Volumes of 10 ul were applied to the inner and outer surfaces of the ear. Each mouse received 2 ug/ear TPA. The left ear (control) received acetone delivered in the same manner. The compounds to be evaluated were given orally 30 min after treatment with TPA.

Measurements were taken with Oditest calipers, 0–10 mm with 0.01 graduations. The right and left ears were measured 4 hrs after TPA-induced inflammation.

The difference between right and left ear thickness was calculated and the significance was determined by a one way analysis of variance with Dunnet's comparisons to control (P=0.05). Drug effects are expressed as a percent change from control values according to the following formula.

% change from control =

$$\frac{(Rt.\ ear - Lt.\ ear)drug - (Rt.\ ear - Lt.\ ear)control}{(Rt.\ ear - Lt.\ ear)control} \times 100$$

In this test procedure, BW755c has an oral $ED_{50}$ of 88 mg/kg, phenidone has an oral $ED_{50}$ of 235 mg/kg, and indomethacin was inactive at 10 mg/g. The following results were obtained for representative compounds of this invention. The results obtained are shown in the table below.

TABLE II

| Compound of Example No. | Dose mg/kg p.o. | Percent Inhibition TPA Ear Edema |
|---|---|---|
| 1 | 80 | 19 |
|   | 160 | 49 |
| 2 | 80 | 21 |
|   | 160 | 66 |

These results show that the compounds of this invention inhibited dermal inflammation in response to an inflammatory challenge, and are therefore useful as antiinflammatory agents.

What is claimed is:
1. A compound having the formula wherein $R^1$ is hydrogen, alkyl of 1–10 carbon atoms, cycloalkyl of 1–10 carbon atoms, arylalkyl of 4–10 carbon atoms, $-(CH_2)_rCH=CH_2$, $-(CH_2)_sOY$, $-(CH_2)_tCH(OZ)CH_3$, or Ar;

X is $NR^2$;

Y and Z are each, independently, hydrogen, alkyl of 1–6 carbon atoms, or $-COR^3$;

$R^2$ and $R^3$ are each, independently, hydrogen, alkyl of 1–6 carbon atoms, or arylalkyl of 4–10 carbon atoms;

Ar is an aryl radical that may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoroalkoxy of 2–7 carbon atoms, amino, dialkylamino of 1–6 carbon atoms per alkyl group, dialkylaminoalkyl of 1–6 carbon atoms per alkyl group, hydroxyalkyl of 1–6 carbon atoms, alkoxyalkyl of 2–12 carbon atoms, alkylthio of 1–6 carbon atoms, $-SO_3H$, $-PO_3H$, and $-CO_2H$;

m=1–5;
n=0–1;
p=1–9;
r=0–6;
s=2–6; and
t=0–6 or a pharmaceutically acceptable salt thereof.

2. The compound of claim 1 wherein m=1–3 and p=1–4 or a pharmaceutically acceptable salt thereof.

3. A method of treating an inflammatory condition in a mammal which comprising to said mammal an antiinflammatory effective amount of a compound having the formula wherein $R^1$ is hydrogen, alkyl of 1–10 carbon atoms, cycloalkyl of 1–10 carbon atoms, arylalkyl of 4–10 carbon atoms, $-(CH_2)_rCH=CH_2$, $-(CH_2)_sOY$, $-(CH_2)_tCH(OZ)CH_3$, or Ar;

X is $NR^2$;

Y and Z are each, independently, hydrogen, alkyl of 1–6 carbon atoms, or $-COR^3$;

$R^2$ and $R^3$ are each, independently, hydrogen, alkyl of 1–6 carbon atoms, or arylalkyl of 4–10 carbon atoms;

Ar is an aryl radical that may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoroalkoxy of 2–7 carbon atoms, amino, dialkylamino of 1–6 carbon atoms per alkyl group, dialkylaminoalkyl of 1–6 carbon atoms per alkyl group, hydroxyalkyl of 1–6 carbon atoms, alkoxyalkyl of 2–12 carbon atoms, alkylthio of 1–6 carbon atoms, $-SO_3H$, $-PO_3H$, and $-CO_2H$;

m=1–5;
n=0–1;
p=1–9;
r=0–6;
s=2–6; and
t=0–6 or a pharmaceutically acceptable salt thereof.

4. A pharmaceutical composition which comprises a compound having the formula wherein $R^1$ is hydrogen, alkyl of 1–10 carbon atoms, cycloalkyl of 1–10 carbon atoms, arylalkyl of 4–10 carbon atoms, $-(CH_2)_rCH=CH_2$, $-(CH_2)_sOY$, $-(CH_2)_tCH(OZ)CH_3$, or Ar;

X is $NR_2$;

Y and Z are each, independently, hydrogen, alkyl of 1–6 carbon atoms, or $-COR^3$;

$R^2$ and $R^3$ are each, independently, hydrogen, alkyl of 1–6 carbon atoms, or arylalkyl of 4–10 carbon atoms;

Ar is an aryl radical that may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoroalkoxy of 2–7 carbon atoms, amino, dialkylamino of 1–6 carbon atoms per alkyl group, dialkylaminoalkyl of 1–6 carbon atoms per alkyl group, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$;

$m=1–5$;
$n=0–1$;
$p=1–9$;
$r=0–6$;
$s=2–6$; and
$t=0–6$ or a pharmaceutically acceptable salt thereof, and a pharmaceutical carrier.

* * * * *